United States Patent
Maierhofer

(10) Patent No.: US 10,349,876 B2
(45) Date of Patent: Jul. 16, 2019

(54) DIALYSIS MACHINE HAVING THE CAPABILITY OF DETERMINING A PREDIALYTIC PROPERTY IN THE BLOOD OF A DIALYSIS PATIENT

(71) Applicant: FRESENIUS MEDICAL CARE DEUTSCHLAND GMBH, Bad Homburg (DE)

(72) Inventor: Andreas Maierhofer, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 111 days.

(21) Appl. No.: 15/504,918

(22) PCT Filed: Aug. 17, 2015

(86) PCT No.: PCT/EP2015/001690
§ 371 (c)(1),
(2) Date: Feb. 17, 2017

(87) PCT Pub. No.: WO2016/026569
PCT Pub. Date: Feb. 25, 2016

(65) Prior Publication Data
US 2017/0265793 A1    Sep. 21, 2017

(30) Foreign Application Priority Data
Aug. 20, 2014    (DE) .................. 10 2014 012 423

(51) Int. Cl.
*A61B 5/145*    (2006.01)
*A61M 1/16*    (2006.01)
(Continued)

(52) U.S. Cl.
CPC ........ *A61B 5/14546* (2013.01); *A61B 5/7221* (2013.01); *A61M 1/1607* (2014.02);
(Continued)

(58) Field of Classification Search
CPC . A61B 5/14546; A61B 5/1468; A61B 5/7221; A61M 1/1607; A61M 1/1609;
(Continued)

(56) References Cited

U.S. PATENT DOCUMENTS

| 4,923,613 A * | 5/1990 | Chevallet ................ A61M 1/16 210/647 |
| 2012/0018379 A1 * | 1/2012 | Gross ...................... A61M 1/16 210/647 |

FOREIGN PATENT DOCUMENTS

| DE | 102006032926 | 1/2008 |
| EP | 0291421 | 11/1988 |

(Continued)

OTHER PUBLICATIONS

Goureau et al. Evaluation of plasma sodium concentration during hemodialysis by computerization of dialysate by computer of dialysate conductivity. Asaio Transactions, Bd. 36, Nr. 3, Jul. 1, 1990.
(Continued)

*Primary Examiner* — John Kim
(74) *Attorney, Agent, or Firm* — Jacobson Holman, PLLC.

(57) ABSTRACT

The invention relates to a dialysis machine having the capability of determining a predialytic property in the blood of a dialysis patient which has an extracorporeal blood circuit, a dialyzate circuit, a dialyzer and a processing unit, wherein at least one sensor for determining a property of the dialyzate is arranged in the dialyzate circuit. The processing unit is configured such that temporal evaluation ranges are fixed during an initial phase of the dialysis treatment, in which temporal evaluation ranges all stability criteria from a predefined group are satisfied; and in that only measured values determined by the at least one sensor within these
(Continued)

temporal evaluation ranges are used for determining a predialytic property of the patient's blood.

18 Claims, 3 Drawing Sheets

(51) Int. Cl.
    *A61B 5/00*     (2006.01)
    *A61B 5/1468*     (2006.01)

(52) U.S. Cl.
    CPC ........ *A61M 1/1609* (2014.02); *A61M 1/1613* (2014.02); *A61B 5/1468* (2013.01); *A61M 2205/3317* (2013.01); *A61M 2205/52* (2013.01); *A61M 2230/20* (2013.01)

(58) Field of Classification Search
    CPC ........ A61M 1/1613; A61M 2205/3317; A61M 2205/52; A61M 2230/20
    See application file for complete search history.

(56) References Cited

FOREIGN PATENT DOCUMENTS

| | | |
|---|---|---|
| EP | 1062960 | 12/2000 |
| EP | 1108438 | 6/2001 |
| EP | 2413991 | 2/2012 |
| WO | WO 2010112223 | 10/2010 |

OTHER PUBLICATIONS

Fresenius Medical Care: Online Clearance Monitoring—Dialyseeffektivitat wird messbar—Impulse fur mehr Lebensqualitat. Bad Homburg, 2008.

* cited by examiner

DIALYSIS MACHINE HAVING THE CAPABILITY OF DETERMINING A PREDIALYTIC PROPERTY IN THE BLOOD OF A DIALYSIS PATIENT

The invention relates to a dialysis machine having an extracorporeal blood circuit, a dialyzate circuit, a dialyzer and a processing unit, wherein at least one sensor is arranged in the dialyzate circuit for determining a property of the dialyzate. The processing unit has the capability of estimating a predialytic property in the blood of a dialysis patient.

The sodium ion concentration in the blood plasma of a dialysis patient is an important diagnostic parameter which can prompt the physician to further examinations as well as to adaptations both of the dialysis regime and of the medication treatment (e.g. using diuretics, for glycemia checking, etc.). In addition, mortality and morbidity correlate with the variability of the predialytic sodium ion concentration in the blood plasma. Blood analyses for determining the sodium ion concentration in the blood plasma are complex and expensive and are therefore hardly carried out with sufficient frequency.

Approximations of the predialytic sodium ion concentration in the blood plasma from conductivity measurements in the dialyzate during the dialysis are known from the prior art which are admittedly possible without additional effort, but which are imprecise and only give an approximation for a time at which the sodium ion concentration in the blood plasma has already changed substantially under the influence of the dialysis.

These methods are based on the fact that the electrolytes in the blood are in balance with those in the dialyzate via the contact in the dialyzer on a dialysis treatment. Due to the conservation of mass, with knowledge of the substance concentrations $\hat{c}_{di}$ and $\hat{c}_{do}$ on the dialyzate side upstream and downstream of the dialyzer, of the dialyzate flow through the dialyzer $Q_d$, of the substituate flow $Q_s$, of the UF rate $Q_f$ and of the clearance K, it is possible to calculate the substance concentration $\hat{c}_{bi}$ on the blood inlet side. In M. Gross et al., "Online clearance measurement in high-efficiency hemodiafiltration", Kidney International, 72, p. 1550 ff. a general formulate is given on the mass balance in HD and HDF treatments:

$$\hat{c}_{do}(t) = \left(1 - \frac{K}{Q_d + Q_s + Q_f}\right)\hat{c}_{di}(t) + \frac{K\hat{c}_{bi} - \frac{d}{dt}M(t)}{Q_d + Q_s + Q_f} \quad [1]$$

Conversion after $c_{bi}$ produces in the stationary state d/dt M(t)=0:

$$\hat{c}_{bi} = \hat{c}_{di} + \frac{Q_d + Q_s + Q_f}{K}(\hat{c}_{do} - \hat{c}_{di}) \quad [2]$$

The concentration of sodium ions in the dialysis liquid $\hat{c}_d^{Na}$ correlates strongly with the temperature-compensated conductivity $c_d$ of the dialysis fluid.

In dialyzers with the option of a conductivity-based clearance measurement, the conductivity of the dialyzate can be measured continuously upstream and downstream of the dialyzer. In this respect, a storage of the conductivity values $c_{di}(t_i)$ and $c_{do}(t_i)$ in a storage unit can take place simultaneously at equidistant times $t_i$. Dialyzers having the capability of a conductivity-based clearance measurement are disclosed, for example, in EP 2 413 991 A1 or EP 1 108 438 B1. There are furthermore dialyzers which have the capability of storing the dialyzate flow $Q_d(t_i)$, the blood flow $Q_b(t_i)$, the substituate flow $Q_s(t_i)$ and the ultrafiltration rate $Q_f(t_i)$ at the times $t_i$ and further subsequently of determining the clearance $K(t_i)$ at any time $t_i$. Such a dialyzer is disclosed, for example, in EP 1 062 960 B1. The equivalent conductivity $c_{bi}(t_i)$ at the blood inlet can thus be calculated at the time $t_i$:

$$c_{bi}(t_i) = c_{di}(t_i) + \frac{Q_d(t_i) + Q_s(t_i) + Q_f(t_i)}{K(t_i)}(c_{do}(t_i) - c_{di}(t_i)) \quad [3]$$

In practice, the determination of $c_{bi}(t_i)$ is, however, not possible with a meaningful precision for various reasons. For, on the one hand, there is only contact between blood and dialyzate after a connection of the patient via the dialyzer so that there is a relationship between $c_{do}$ and $c_{bi}$. The calculated $c_{bi}$ is therefore either equal to $C_{di}$ directly after the start of the dialysis (if an equilibration has taken place between the dialysis fluid and the blood-side cleaning solution in the preparation phase) or it contains an arbitrary value from the time in which the blood and the cleaning solution mix after the connecting of the patient for so long until a detector located at the blood-side return line detects the presence of blood.

If a constant flow time $t_F$ between the conductivity sensors determining $c_{di}$ and $c_{do}$ is taken into account and $c_{bi}$ is calculated according to $$c_{bi}(t_j) = c_{di}(t_j) + \frac{Q_d(t_j) + Q_s(t_j) + Q_f(t_j)}{K(t_j)}(c_{do}(t_j) - c_{di}(t_i))$$

where $t_j=t_i+t_F$, variations in $c_{di}$ are hereby better taken into account which have a time offset effect on $c_{do}$. See in this connection the comparison of the curves $c_{bi}(t_F)$ and $c_{bi}$ in FIG. 1.

Particularly at the start of the treatment, however, $c_{di}$ and $c_{do}$ are unstable. The conductivity $c_{di}$ varies, for example, due to the change in the bicarbonate concentration after the end of the bicarbonate reduction in the preparation (cf. FIG. 2, Field No. 1, where the change in $c_{di}$ as a consequence of the change in the bicarbonate concentration in the dialyzate from 24 to 32 mmol/l can be recognized) or due to adjustment by the user or automated regulations of the sodium ion concentration in the dialyzate. The conductivity $c_{do}$ is influenced by the coupling with the patient's blood. Particularly at the start of the dialysis, larger concentration changes take place in this respect due to diffuse exchange since the largest gradients are present at this time. Infusion of cleaning solution on the connecting or later medication administration into the blood hose system likewise result in short-term changes of $c_{do}$. Due to the inertia of the system, changes in the pump rates (e.g. change of the blood pump rate by the user or in an automated fashion for optimizing the blood flow while taking account of the arterial pressure and the venous pressure, adaptations of the substituate rate by the user or by automated regulations, pump variations or pump stops in the automated carrying out of system tests, etc.) result in time-delayed fluctuations in $c_{do}$ (cf. FIG. 2, Field No. 2, where the change of blood flow, dialyzate flow and substituate flow at the start of the treatment is shown; and FIG. 2, Field No. 3, where the automated change of the substituate flow through the machine is shown). Self-tests of the machine and by-pass circuits in which the dialyzate flow is conducted past the dialyzer prevent the determination of $c_{bi}$ (cf. FIG. 2, Field No. 4) due to the lack of a coupling to the patient's blood and the instabilities caused by it. A determination of $c_{bi}$ is also not possible during ongoing conductivity variations for determining the clearance (for example by OCM, Diascan or the like; cf. FIG. 2, Field No. 5). Changes to the clearance $K(t_j)$ caused by the change in the flow parameters also result in fluctuations in $c_{bi}$.

If no $c_{bi}$ is calculated as described above, the named instabilities thus result in fluctuations in the calculated $c_{bi}$ in the first 10 min of the dialysis which can easily correspond to concentration fluctuations of more than 5 mmol/l (see in this connection the comparison of the curves $c_{bi}(t_F)$ and $C_{bi}$ in FIG. 1). The value thus determined can thus not be used as an input value for the determination of a surrogate for the predialytic sodium ion concentration in the blood plasma of the dialysis patient or its fluctuation.

It is therefore the underlying object of the present invention to find a possibility of being able to provide a surrogate for the predialytic ion concentration, preferably the sodium ion concentration, in the blood plasma without additional costs in any dialysis treatment with sufficient precision.

Against this background, the invention relates to a dialysis machine having an extracorporeal blood circuit, a dialyzate circuit, a dialyzer and a processing unit, wherein at least one sensor is arranged in the dialyzate circuit for determining a property of the dialyzate. Provision is made in accordance with the invention that the processing unit is configured such that temporal evaluation ranges are fixed during an initial phase of the dialysis treatment in which all stability criteria from a predefined group are satisfied. In accordance with the invention, the processing unit is further configured such that the concentration determined by the at least one sensor is used for determining a predialytic property of the patient's blood, wherein only those measured values are considered in this determination which were determined within these temporal evaluation ranges.

Temporal ranges within the initial phase of the dialysis treatment which lie outside the temporal evaluation ranges are therefore not used for the determination of the predialytic property of the patient's blood. The invention therefore makes provision that not all measured values determined in the initial phase of the dialysis treatment are used, but only some of these measured values (for example less than 60%, 50% or 40% of the measured values determined during the initial phase of the dialysis treatment). Temporal ranges outside the initial phase of the dialysis treatment are preferably not used for the determination of the predialytic property of the patient's blood.

According to the current prior art and to the typical practice in dialysis operation, both the sodium ion concentration in the blood plasma of the patient with respect to other electrolytes is a preferred value and the determination thereof by conductivity measurements is a preferred method. Provision is made to this extent in an embodiment that the dialysis machine comprises a first conductivity sensor upstream of the dialyzer and a second conductivity sensor downstream of the dialyzer and that determined measured values of the conductivity of the dialyzate upstream of the dialyzate and downstream of the dialyzer are used for the determination of the predialytic ion concentration in the blood plasma of the dialysis patient, wherein only those measured conductivity values are considered in this determination which were determined within the temporal evaluation ranges. The predialytic ion concentration in the blood plasma of the dialysis patient to be determined is preferably the predialytic sodium ion concentration in the blood plasma of the dialysis patient. The determination of other predialytic ion concentrations in the blood plasma of the patient, for example the potassium ion concentration, is also conceivable within the framework of the inventive concept.

The method in accordance with the invention described in the above-named embodiment and in the embodiments for sodium and conductivity measurements can, however, also be extended to all other substances in which blood-side values can be concluded from a dialyzate-side concentration measurement with a known clearance. Corresponding sensors are then required for this purpose.

In accordance with the invention, a determination of the predialytic property of the patient's blood takes place in an initial phase of the treatment in which changes of, for example, the ion concentration in the blood plasma of the dialysis patient can have taken place either only within a limited range or in a largely predictable manner for physiological considerations. In this respect, ranges in the course of treatment in which no reliable determination of the predialytic property of the patient's blood is possible are not considered in the evaluation. An increased precision is thereby achieved.

In an embodiment, measured values from a plurality of temporal evaluation ranges, and preferably from all temporal evaluation ranges, are used for the calculatory estimation of the predialytic property of the patient's blood. A greater precision can thus be achieved within the framework of a regressive determination (described in more detail below) of the predialytic property of the patient's blood.

The initial phase of the dialysis treatment can end after the end of a preset treatment duration (the dialysis treatment starts as soon as blood circulates through the extracorporeal blood circuit and is contacted by dialyzate in the dialyzer). It is furthermore conceivable that the initial phase of the dialysis treatment ends when a specific treatment efficiency is reached (for example a Kt/V value of 0.3). Exemplary values comprise a duration of the initial phase of 30 minutes, 20 minutes, 10 minutes or 5 minutes. The underlying consideration is that the initial phase of the dialysis treatment is determined from the time within which the changes of, for example, the ion concentration in the blood of the dialysis patient may have taken place either only within a limited range or in a largely predictable manner for physiological considerations. This time can be selected in general or in a patient-specific manner according to empirical values.

The predefined group of stability criteria comprises at least one stability criterion and preferably a plurality of stability criteria.

Suitable stability criteria can be obtained, for example, by the comparison of a value determined by measurement with a threshold value. An example is the fluctuation of the conductivity of the dialyzate upstream and/or downstream of the dialyzer. A further example is the change rate of the conductivity of the dialyzate upstream and/or of the dialyzer (expressed e.g. as a straight line increase in the conductivity/time diagram). For example, the standard deviation and/or change rate (for example, using the measured values of the past 30 or 60 seconds) can be compared with a threshold value. If the standard deviation and/or change rate is lower than the threshold value, this stability criterion is satisfied and the time in which the most recent measured values were obtained (e.g. the past 30 or 60 seconds) falls within a temporal evaluation range, subject to the satisfaction of some further stability criteria. The measured values obtained in this time period are used for determining the predialytic ion concentration in the blood plasma of the dialysis patient. If the standard deviation and/or change rate is higher than the threshold value, this stability criterion is not satisfied and the time in which the most recent measured values were obtained falls outside the temporal evaluation range. The measured values are not used for the determination.

The time interval from specific events is furthermore suitable as a stability criterion. A stability criterion can be satisfied, for example, if a specific blocked time after a specific event has ended. The blocked time falls outside the temporal evaluation range. The measured values obtained in this time period are not used for determining the predialytic ion concentration in the blood plasma of the dialysis patient. The measured values obtained after the end of the blocked time are used for the estimation subject to the satisfaction of some further stability criteria.

Examples for events which can trigger a blocked time comprise changes in the dialyzate flow, of the blood flow, of the substituate flow, of the UF rate, of the dialyzate composition (sodium ion concentration or bicarbonate concentration, change of the concentrate, etc.). The changes can be caused by changed presets by the user or by automated settings. Further examples for events which can trigger a blocked time comprise bypass switchovers and pump stops, for example in infusion of cleaning solution into the extracorporeal blood circuit, self-tests of the system (pressure holding test) or as a consequence of user actions (opening of doors and covers). The blocked time can amount to less than 2 minutes, for example between 15 and 90 seconds or between 30 and 60 seconds. It can be selected differently for different events. The blocked time after a bypass switchover can, for example, amount to 60 seconds, and after a change of the dialyzate flow to 30 seconds. The degree of change can also be taken into account (e.g. 30 seconds on a change of the dialyzate flow by less than 300 ml/min and 60 seconds on a change by more than 300 ml/min).

Against the initially named background, the invention furthermore relates to a dialysis machine having an extracorporeal blood circuit, a dialyzate circuit, a dialyzer and a processing unit, wherein a first sensor is arranged upstream of the dialyzer in the dialyzate circuit and a second sensor is arranged downstream of the dialyzer. In accordance with the invention, the processing unit is configured such that determined measured values upstream of the dialyzer at a first time and downstream of the dialyzer at a later second time are used as corresponding value pairs for determining a predialytic property of the patient's blood, wherein the time offset between the first and second times is approximated to the flow time of the dialyzate between the first sensor and the second sensor or corresponds thereto.

To the extent, in accordance with the invention, the flow time of the dialyzate between the two conductivity sensors is taken into account in the determination of the predialytic property of the patient's blood. If larger fluctuations occur in the conductivity of the dialysis solution, an error in the determination of the predialytic property of the patient's blood can arise due to the time offset which the dialysis solution requires to run through the dialyzer because the difference no longer correctly reflects the concentration change in the filter. This error is reduced by the consideration of the flow time.

In an embodiment, the first and second sensors are conductivity sensors and the processing unit is configured such that the determined measured values are the conductivities of the dialyzate upstream and downstream of the dialyzer and such that these conductivities are used as corresponding value pairs for determining the predialytic ion concentration, preferably the sodium ion concentration, in the blood plasma of the dialysis patient.

Provision is made in an embodiment that the measure in accordance with the invention of taking account of the flow time of the dialyzate between the two sensors and the measure in accordance with the invention of the selection of temporal evaluation ranges within the initial treatment phase with reference to stability criteria are used in combination.

The time offset is preferably adapted, provided that the flow speed of the dialyzate changes in the course of the treatment.

The time offset can be calculated in an embodiment from the volume of the hydraulic system between the two sensors (volume of the line sections and of the dialyzate chamber of the dialyzer) and the dialyzate flow in volume per time.

Alternatively, the time offset can be determined from the time difference between the detection of a disturbance (for example a brief concentration increase) at the first and second sensors. Provision can be made in this case that no new determination of the time offset by detection of a disturbance takes place after a change of the flow speed of the dialyzate, but that rather the time offset is updated by extrapolation while taking account of the old and new flow speeds.

Provision is made in an embodiment for determining the predialytic ion concentration in the blood plasma of the dialysis patient that a predialytic plasma-equivalent conductivity is determined using the conductivity values determined upstream and downstream of the dialyzer and that further subsequently the ion concentration in the plasma of the dialysis patient is determined from the predialytic plasma-equivalent conductivity. This can take place using the mathematical operations named initially and further subsequently in the embodiment.

Provision is made in an embodiment for determining the predialytic ion concentration in the blood plasma of the dialysis patient that the predialytic plasma-equivalent conductivity is determined by extrapolation of instantaneous plasma-equivalent conductivities which are determined for the temporal evaluation ranges and/or while taking account of the time offset from the conductivity values upstream and downstream of the dialyzer. In this respect, a time-dependent interpolation can, for example, be provided, with the regression of the data being able to take place as a function of the time on a polynomial of the order n. Preferred orders are n=0 (mean value formation) and n=1 (linear regression). Another possibility is the use of a non-linear function, e.g. in the modeling of an exponential increase or drop in the sodium ion concentration as a function of time. Instead of a time-dependent interpolation, an interpolation can also be provided which is based on a different parameter, for example on a regression of the data as a function of the Kt/V value. This can take place using the mathematical operations named initially and further subsequently in the embodiment.

Alternatively, it is conceivable for determining the predialytic ion concentration in the blood plasma of the dialysis patient that the predialytic ion concentration is determined by extrapolation of instantaneous ion concentrations which are determined for the temporal evaluation ranges and/or while taking account of the time offset from the conductivity values upstream and downstream of the dialyzer.

The invention further relates to a dialysis method which can be carried out using a dialysis machine in accordance with the invention and which works through the steps of the routine stored in the processing unit.

The dialysis machine in accordance with the invention can, for example, be one for hemodialysis, for hemodiafiltration or for hemofiltration.

BRIEF DESCRIPTION OF THE DRAWINGS

Further details and advantages of the invention result from the enclosed Figures and with reference to the embodiments described in the following. There are shown in the Figures:

FIG. 3 shows schematic representation of an embodiment of a dialysis machine in accordance with the invention with the capability of estimating the predialytic sodium ion concentration in the blood plasma of a dialysis patient.

Figure 1:
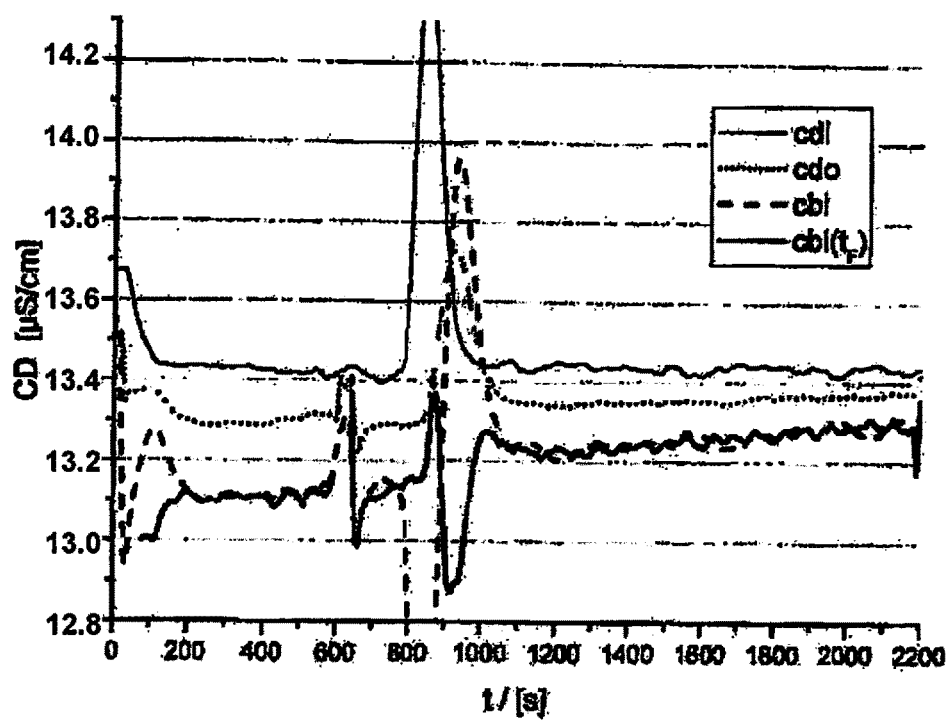
FIG. 1: a diagram of the calculated plasma conductivity with and without consideration of the flow time $t_F$.
Figure 2:
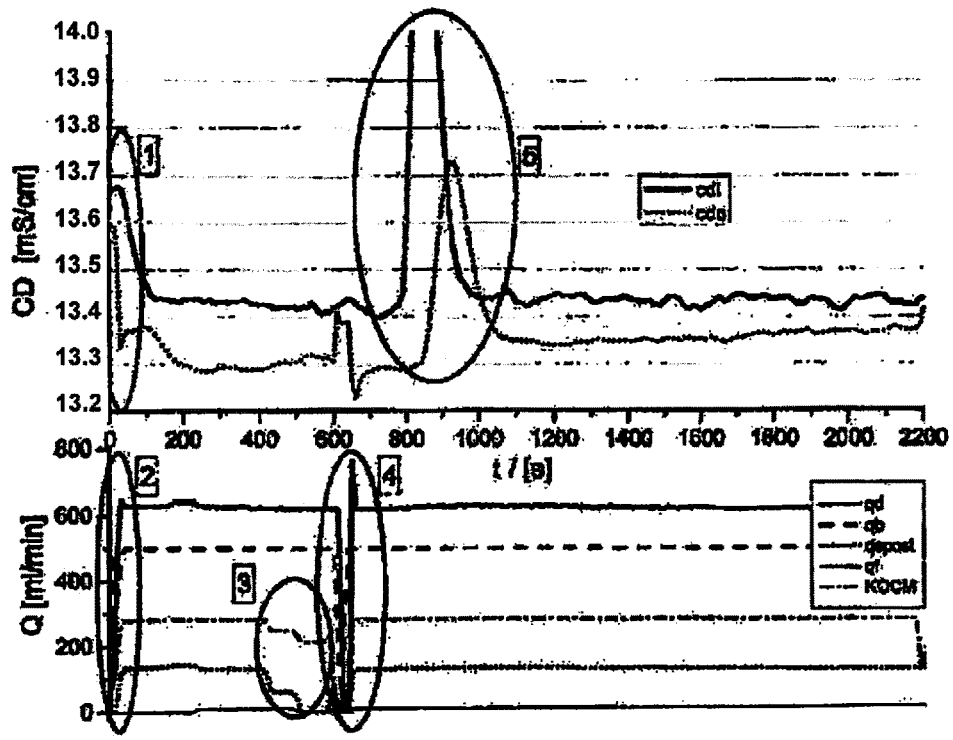
FIG. 2: a diagram of the time curve of conductivities, flows and calculated clearance.
Figure 3:
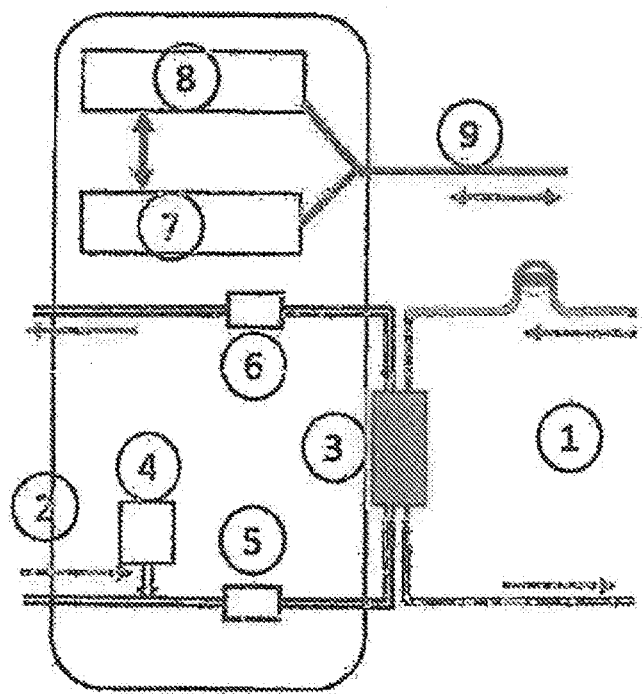
FIG. 3: a schematic representation of a dialysis machine in accordance with the invention with the capability of estimating the predialytic sodium ion concentration in the blood plasma of a dialysis patient.

In this respect, a blood circuit 1 is in communication with a dialyzate circuit 2 via a dialyzer 3. The dialyzate circuit 2 comprises a concentrate metering unit 4 as well as pumps, valves and sensors not shown in more detail in the Figure. The measurement of the temperature-compensated dialyzate-side conductivity upstream and downstream of the dialyzer takes place using first and second conductivity cells 5 and 6. Flow sensors and the conductivity cells communicate measured data continuously to the processing unit 7. The algorithms described further subsequently for determining the predialytic sodium ion concentration in the blood plasma of the dialysis patient are stored in said processing unit. The processing unit 7 is in communication with a user interface 8 for reporting to the user. Data from the processing unit 7 or from the user interface 8 can be transmitted via a data network 9 to an external computer for further storage and processing.

The algorithm stored in the processing unit 7 comprises the following elements:

Calculating $c_{bi}$ While Taking Account of the Delay Time $t_F$.

The delay time $t_F(Q_d)$ can be calculated directly with knowledge of the hydraulic properties of the system between the conductivity cells 5 and 6 and the dialyzate flow with a constant dialyzate flow $Q_d$. The delay occurring in the dialyzer 6 due to its volume can be seen from the dialyzer type which either manually or automatically (e.g. by marking the dialyzer using an RFID tag or by a barcode and reading by a corresponding unit). Alternatively, $t_F$ can take place from the time delay of the response in $c_{do}$ to a conductivity change in $c_{di}$ (e.g. conductivity pulse for determining the clearance, cf. FIG. 1). If $Q_d(t_j)$ differs at a time $t_j$ from the dialyzate flow present on the determination of $t_F$ at the time $t_M$, $t_F Q_d(t_j)$ can be determined by extrapolation, e.g. by $$t_F(t_j) = t_F \frac{Q_d(t_M)}{Q_d(t_j)}. \quad [5]$$

Subsequently, $c_{bi}$ is calculated according to the initially shown formula 4. It must be taken into account in this respect that the storage of the relevant data only takes place at time intervals $\Delta t_s$ for reasons of capacity. An improvement in the calculation of $c_{bi}$ can therefore be achieved by a shortening of $\Delta t_s$ in the time interval required for the calculation of the initial plasma Na to an acceptable minimum. Alternatively, an interpolation of intermediate value for $c_{bi}$ can take place on the basis of the adjacent stored data.

Elimination of Ranges in Which No Reliable Calculation of $C_{bi}$ is Possible.

Time ranges in which what was calculated as described above does not correspond to the real value due to different stability criteria are not taken into account for the further evaluation. They include the following stability criteria:

changes in the presets by the user or by automatic settings of dialyzate, blood flow and substituate flow as well as of the ultrafiltration rate or of the dialyzate composition (desired values for sodium and bicarbonate, change of the concentrate, etc.);

bypass switchovers and pump stops in self-tests of the system or as a consequence of user actions (e.g. opening of doors and covers).

On changes, $c_{bi}$ is marked as invalid for a duration $t_{D\_change,j}$ from the time of the change. $t_{D\_change,j}$ is stored in the processing unit 7 and can adopt different values depending on the disturbance (e.g. 1 minute after the bypass switchover, 30 seconds after a change of the blood pump rate). Rules can also be stored according to which $t_{D\_change,j}$ depends on the degree of the change of a parameter (e.g. 30 seconds on a change of the dialyzate flow by 100 ml/min, 60 seconds on a change by >300 ml/min).

Furthermore, an insufficient stability of $c_{di}$ and $c_{do}$ can be used as a trigger for a blocking time $t_{D\_stab,j}$. $c_{bi}$ can thus be marked as invalid for so long until a sufficient stability is again present. The following stability criteria for instability can be applied in this respect:

fluctuation of the LF ($c_{di}$ or $c_{do}$), expressed e.g. as a standard deviation above a predefined threshold value;

change rate of the LF, expressed e.g. as a straight line increase, above a predefined threshold value.

Figure 4:
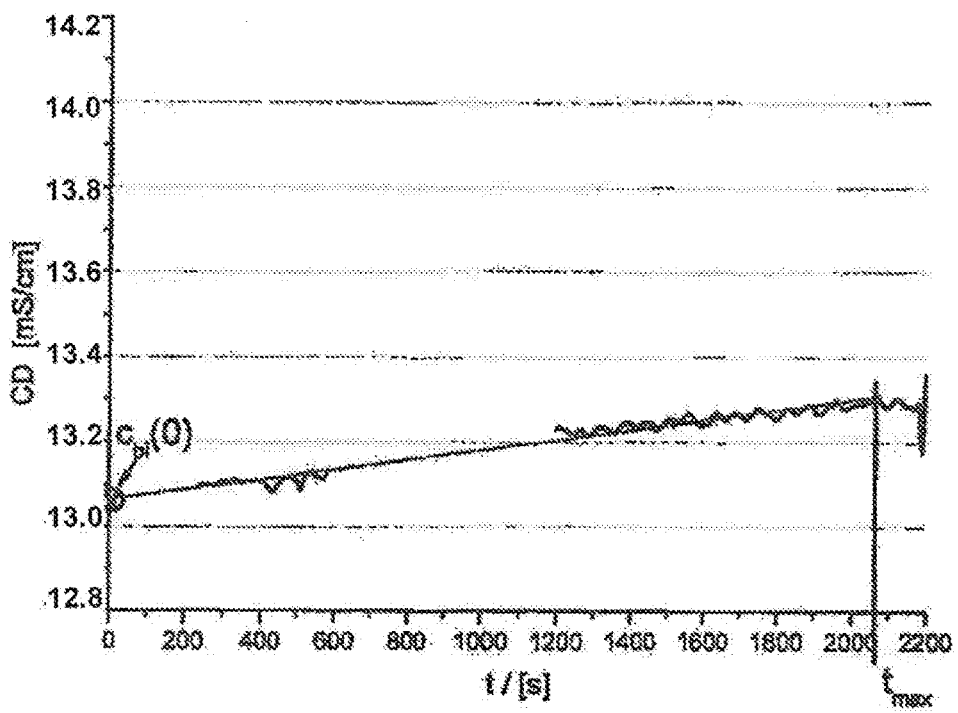
FIG. 4: a diagram which shows a fit of the plasma conductivity when applied against the treatment duration.

After eliminating the values of $c_{bi}$ marked as invalid, the values which can be used for the further evaluation remain in the memory of the processing unit (cf. FIG. 4, solid line).

Extrapolation of $c_{bi}$ to the Predialytic Value

For the extrapolation of $c_{bi}$ to the predialytic value, all remaining values of $c_{bi}$ up to a maximum initial dialysis duration $t_{max}$ are used. The maximum initial dialysis duration $t_{max}$ is determined from the time within which the changes in the concentration of the sodium ions in the blood plasma of the dialysis patient for physiological considerations can have taken place either only within a limited range or in a largely predictable manner, e.g. on modeling the mass transfer between the blood and the dialyzate by a 1-pool model as in formula 6 shown below:

$$c_{bi}(t) = c_{di} + (c_{bi}(0) - c_{di})e^{-\frac{Kt}{V}} \quad [6]$$

The maximum initial dialysis duration $t_{max}$ can in this respect e.g. be a fixed time, e.g. 30 minutes, or the time up to which a specific treatment efficiency, e.g. Kt/V=0.3, is reached.

The interpolation then takes place e.g. by regression with a polynomial of the order n. Preferred orders are n=0 (mean value formation) and n=1 (linear regression) with the remaining sampling points (cf. FIG. 4, dotted line). Another option is the extrapolation by means of a non-linear function, e.g. the modeling of an exponential increase or drop of $c_{bi}$.

Figure 5:
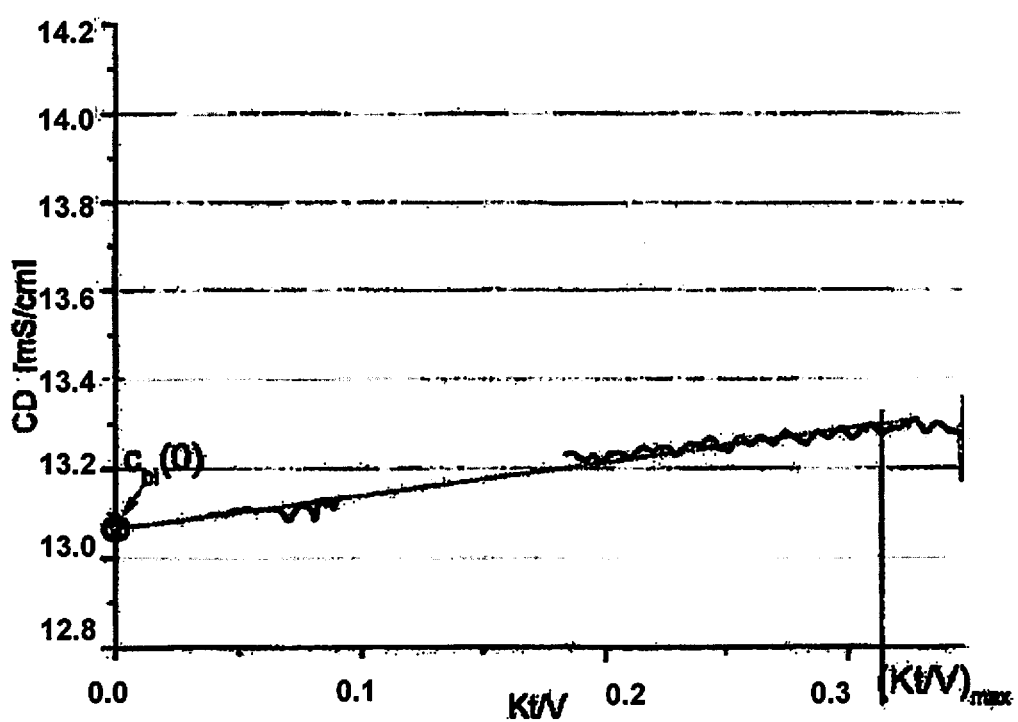
FIG. 5: a diagram which shows a fit of the plasma conductivity when applied against the dialysis dosage Kt/V.

Instead of a temporal interpolation, an interpolation can also take place on the basis of a model for the change of $c_{bi}$ as in Formula 6 (cf. FIG. 5). A polynomial-based regression is also possible here: It applies in a first approximation: $e^{-x} \approx 1-x$, where the deviation for x<0.3 amounts to less than 5%. It thus applies to Kt/V<0.3 in a good approximation:

$$c_{bi}(t) = c_{bi}(0) + (c_{di} - c_{bi}(0))\left(\frac{Kt}{V}\right) \quad [7]$$

$c_{bi}(0)$ can thus also be determined by a linear fit of an application against Kt/V (cf. FIG. 5). Changes in the flows determining the clearance can hereby be determined better.

Conversion to the Predialytic Sodium Ion Concentration in the Blood Plasma of the Dialysis Patient The predialytic plasma-equivalent conductivity $c_{bi}(0)$ determined as described above can now be converted by means of a model for the relationship between temperature-compensated conductivity and electrolyte composition to a predialytic sodium ion concentration in the blood plasma of a dialysis patient $\hat{c}^{Na}_{bi}(0)$.

$$\hat{c}^{Na}_{bi}(0) = f(c_{bi}(0), \tilde{c}^j_{bi}(0)) \quad [8]$$
$$= a_0 + a_1 c_{bi}(0) + \sum_j b_j \tilde{c}^j_{bi}(0)$$

$\hat{c}^j_{bi}(0)$ designates the concentration of electrolytes other than Na, e.g. potassium, which have an influence on the conductivity. Their concentration can be determined by the user by a blood analysis and can be input manually via the user interface 8 or via a data link 9 with an external memory medium or a database. A higher precision can be achieved with knowledge of $\hat{c}^j_{bi}(0)$, with the adopting of standard values generally being sufficient. The factors $a_0$, $a_1$ and $b_j$ are in this respect fixedly stored in the processing unit.

Storage and Trend Analysis

The predialytic sodium ion concentration in the blood plasma of the dialysis patient $\hat{c}^{Na}_{bi}(0)$ can now be displayed at the user interface 8 or can be forwarded via the data link 9 to an external storage medium or to a database. The user can be informed from a trend analysis of the current and past determinations of $\hat{c}^{Na}_{bi}(0)$ of systematic trends of the predialytic sodium ion concentration in the blood plasma of the dialysis patient and its fluctuation. By a comparison of the determined change rate and of the fluctuation of $\hat{c}^{Na}_{bi}(0)$ with stored reference values, the user can be informed of critical values of these parameters on the exceeding of predefined limits.

The dialysis machine in accordance with the invention described in more detail above therefore inter alia comprises the following capabilities for determining the predialytic sodium ion concentration of a dialysis patient due to the algorithm stored in the processing unit and the construction features described further above:

A range in which stable conductivities and dialysis conditions are present can be looked for in the initial phase of the dialysis (e.g. <10 min) by means of the processing unit from data sets stored therein and comprising conductivities and flows and information on disturbances of the dialysis regime (e.g. bypass switchovers). For this purpose, different stability criteria (e.g. time interval from the last concentration change or change in the pump conveying rate, standard deviation or increase in conductivity) are stored and evaluated in the processing unit. An averaging of $c_{di}$ and $c_{do}$ can take place within this range to reduce fluctuations. The time offset between $c_{di}$ and $c_{do}$ present due to the hydraulic flow paths can be taken into account in that the values of $c_{di}$ at the time t, but of $c_{do}$ at the time $t+t_F$, are used in the calculation of $c_{bi}$, where $t_F$ corresponds to the flow time of the dialyzate between the two conductivity sensors. If a determination of $c_{bi}$ is not possible within the first 5 minutes of the dialysis treatment due to instable dialysis conditions, sampling points can be determined at times of stable dialysis conditions for $c_{bi}$ within the first 30 minutes of the dialysis treatment and an extrapolation to the initial value can be carried out at the start of dialysis. The value of the initial $c_{bi}$ determined in this manner is converted by means of an electrolyte model into a predialytic sodium ion concentration in the blood plasma of the dialysis patient, since $\hat{c}^{Na}_{bi}(0)=f(c_{bi})$. The predialytic sodium ion concentration in the blood plasma of the dialysis patient $\hat{c}^{Na}_{bi}(0)$ can be stored in a patient-specific manner on an internal or external storage medium (patient card, transmission via network, etc.) at the latest at the end of the dialysis treatment. Together with the $\hat{c}^{Na}_{bi}(0)$ from previous treatments, the variability of $\hat{c}^{Na}_{bi}(0)$ can be calculated and provided to the physician as a display parameter. $\hat{c}^{Na}_{bi}(0)$ and its variability can be displayed directly after its calculation instead of at the end of the dialysis. This is generally possible immediately after the first successful OCM measurement (after an approximately 20 minute treatment duration). It can, however, also only be possible later on a delay in the first successful OCM measurement.

According to the current prior art and to the typical practice in dialysis operation, both the predialytic sodium ion concentration in the blood plasma of the dialysis patient with respect to other electrolytes is a preferred value and the determination thereof by conductivity measurements is a preferred method. An embodiment of the dialysis machine in accordance with the invention based thereon was described above. However, the method described for sodium and for the LF measurement can also be extended to all other substances in which a conclusion on blood-side parameters can be drawn from a dialyzate-side concentration measurement with known clearance. Corresponding sensors are then required for this purpose. If the corresponding substance is already present in the inflowing dialyzate, the conductivity sensors 5 and 6 have to be replaced with sensors which specifically determine the concentration of the substance whose predialytic plasma concentration is to be determined. In this respect, e.g., ion-selective electrodes can be used for measuring the concentration of potassium, calcium, magnesium and chloride. However, other measuring methods are also conceivable for measuring electrolytes, e.g. also by NMR. Sensor 5 can be dispensed with if the concentration upstream of the dialyzer is determined in that a bypass switchover takes place at a specific point in time by which the fresh dialyzate can be measured directly by sensor 6, under the condition that it is ensured that the respective concentration during the time required for the determination of the predialytic plasma value does not change substantially. The value in the fresh dialyzate can likewise already be known from manufacturer's data and from an exact knowledge of the mixing system so that a continuous determination upstream of the dialyzer can be dispensed with. Sensor 5 can in particular be omitted with substances which are not present in the fresh dialyzate. With knowledge of the clearance of these substances, e.g. from the conductivity-based determination of the dialyzer clearance and an approximation to the clearance of the corresponding substance by means of a stored correction factor, their predialytic concentration can be determined according to the above-described method. In this respect, sensor 6 can also determine a spectroscopic value such as the absorption or the fluorescence, wherein a calculation process is stored in the evaluation unit which draws a conclusion on substance concentrations from the spectral measurements. Sensors can be used to determine the glucose concentration which determine the rotation of the polarization direction of polarized light on passing through a measurement path containing the sample solution. Alternatively, the change in the refractive index can be determined by refractometry. As above, a calculation process then has to be stored in the evaluation unit with whose aid a conclusion can be drawn on substance concentrations. Fluctuations in the blood glucose can be an important indicator for an insufficient diabetes treatment. Furthermore, instead of the sensors 5 and 6, a plurality of sensors can be used at their positions with whose aid the predialytic concentration of different substances can be determined in accordance with the described method. A predialytic concentration determined for a first parameter can then be used as described above for improving the precision in the determination of the concentration of a further parameter.

In summary, it results that the sodium concentration in the blood plasma is an important diagnostic parameter in dialysis patients. The determination of this value by blood analyses is, however, complex and expensive so that alternatives are being looked for. The calculation of the concentration of different substances in the blood via conductivity measurements on the dialyzate side in the extracorporeal circuit is already described in the prior art. This calculation of the predialytic blood concentration is then based on the extrapolation of the values. Reliable measurements are, however, only present after around 20 minutes from the start of treatment. Measurements at the start of the treatment are subject to large fluctuations which result in larger errors in the concentration determination. These errors are reduced by the invention. In accordance with the invention, ranges in the course of treatment in which no reliable calculation is possible are, on the one hand, not considered in the evaluation. On the other hand, the flow time of the dialyzate between the two conductivity sensors is considered in the calculation of the plasma concentration. The results of the conductivity measurements which take place simultaneously are used in the calculation formula in the prior art. If, however, larger fluctuations occur in the conductivity of the dialysis solution, an error occurs due to the time offset which the dialysis solution requires for running through the filter because the difference no longer correctly reflects the concentration change in the filter. This error is reduced by the consideration of the flow time.

The invention claimed is:

1. A dialysis machine having
   an extracorporeal blood circuit,
   a dialysate circuit,
   a dialyzer,
   a processing unit, and
   at least one sensor for determining a property of the dialysate arranged in the dialysate circuit,
characterized in that the processing unit is configured such that (i) temporal evaluation ranges are fixed during an initial phase of the dialysis treatment to match time periods when all stability criteria from a predefined group are satisfied and (ii) only measured values determined by the at least one sensor within the fixed temporal evaluation ranges are used for determining a predialytic property of the patient's blood.

2. A dialysis machine in accordance with claim 1, characterized in that a first conductivity sensor is arranged upstream of the dialyzer in the dialysate circuit and a second conductivity sensor is arranged downstream of the dialyzer; and in that the processing unit is configured such that measured values of the conductivity value of the dialysate downstream and upstream of the dialyzer determined within the fixed temporal evaluation ranges are used for the determination of a predialytic ion concentration.

3. A dialysis machine in accordance with claim 2, characterized in that the processing unit is furthermore configured such that (i) a predialytic plasma-equivalent conductivity is determined with reference to the conductivity values determined upstream and downstream of the dialyzer and (ii) further subsequently the ion concentration in the plasma of the dialysis patient is determined from the predialytic plasma-equivalent conductivity.

4. A dialysis machine in accordance with claim 3, characterized in that the processing unit is furthermore configured such that the predialytic plasma-equivalent conductivity is determined by extrapolation of instantaneous plasma-equivalent conductivities which are determined for the temporal evaluation ranges and/or while considering the time offset from the conductivity values upstream and downstream of the dialyzer.

5. A dialysis machine in accordance with claim 3, characterized in that the processing unit is furthermore configured such that the predialytic plasma-equivalent conductivity is determined by extrapolation of instantaneous plasma-equivalent conductivities which are determined for the temporal evaluation ranges and/or while considering the time offset from the conductivity values upstream and downstream of the dialyzer, with the extrapolation comprising a regression of the instantaneous plasma-equivalent conductivities as a function of the time or as a function of the Kt/V value.

6. A dialysis machine in accordance with claim 2, characterized in that the processing unit is configured such that determined measured values upstream of the dialyzer at a first time and determined measured values downstream of the dialyzer at a later second time are used as corresponding value pairs for determining a predialytic property of the patient's blood, with the time offset between the first and second times being approximated to the flow time of the dialysate between the first and second sensors or corresponding thereto.

7. A dialysis machine in accordance with claim 1, characterized in that the processing unit is furthermore configured such that measured values from a plurality of the fixed temporal evaluation ranges are used for determining the predialytic property of the patient's blood.

8. A dialysis machine in accordance with claim 1, characterized in that the processing unit is further configured such that the initial phase of the dialysis treatment ends when a preset treatment duration or a preset treatment efficiency has been reached; and/or in that the initial phase of the dialysis treatment ends at the end of the first 30 minutes, 20 minutes, 10 minutes or 5 minutes of the dialysis treatment.

9. A dialysis machine in accordance with claim 1, characterized in that the processing unit is further configured such that a stability criterion is satisfied when the standard deviation and/or change range of the conductivity measured upstream and/or downstream of the dialyzer is smaller than a threshold value stored in the processing unit.

10. A dialysis machine in accordance with claim 1, characterized in that the processing unit is further configured such that a stability criterion is satisfied when a certain blocking time has elapsed after an event from the group change of the dialysate flow, change of the blood flow, change of the substitute flow, change of the UF rate, change of the dialysate composition, bypass switchover, pump stop, infusion of cleaning solution into the extracorporeal blood circuit, self-test of the system, user actions, wherein the blocking time is optionally less than 2 minutes.

11. A dialysis machine in accordance with claim 1, characterized in that a first conductivity sensor is arranged upstream of the dialyzer in the dialysate circuit and a second conductivity sensor is arranged downstream of the dialyzer; and in that the processing unit is configured such that measured values of the conductivity value of the dialysate downstream and upstream of the dialyzer within the fixed temporal evaluation ranges are used for the determination of a predialytic sodium ion concentration.

12. A dialysis machine in accordance with claim 1, characterized in that the processing unit is furthermore configured such that measured values from all the fixed temporal evaluation ranges are used for determining the predialytic property of the patient's blood.

13. A dialysis machine having
an extracorporeal blood circuit,
a dialysate circuit,
a dialyzer,
a processing unit,
a first sensor arranged upstream of the dialyzer in the dialysate circuit, and
a second sensor arranged downstream of the dialyzer,
characterized in that the processing unit is configured such that determined measured values upstream of the dialyzer at a first time and determined measured values downstream of the dialyzer at a later second time are used as corresponding value pairs for determining a predialytic property of the patient's blood, with the time offset between the first and second times being approximated to the flow time of the dialysate between the first and second sensors or corresponding thereto.

14. A dialysis machine in accordance with claim 13, characterized in that the first and second sensors are conductivity sensors; and in that the processing unit is configured such that (i) the determined measured values are the conductivities of the dialysate upstream and downstream of the dialyzer and (ii) the conductivities are used as corresponding value pairs for determining the predialytic ion concentration.

15. A dialysis machine in accordance with claim 13, characterized in that the processing unit is furthermore configured such that (i) the time offset is calculated from the volume of the hydraulic system between the two sensors and the dialysis flow or (ii) the time offset is determined with reference to the time difference between the detection of a disturbance at the first and second sensors.

16. A dialysis machine in accordance with claim 13, characterized in that the processing unit is furthermore configured such that the time offset is adapted, provided that the flow speed of the dialysate changes in the course of the treatment.

17. A dialysis machine in accordance with claim 13, characterized in that the processing unit is furthermore configured such that (i) a predialytic plasma-equivalent conductivity is determined with reference to the conductivity values determined upstream and downstream of the dialyzer and (ii) further subsequently the ion concentration in the plasma of the dialysis patient is determined from the predialytic plasma-equivalent conductivity.

18. A dialysis machine in accordance with claim 13, characterized in that the predialytic ion concentration is the sodium ion concentration, the first and second sensors are conductivity sensors; and in that the processing unit is configured such that the determined measured values are the conductivities of the dialysate upstream and downstream of the dialyzer; and in that the conductivities upstream and downstream of the dialyzer are used as corresponding value pairs for determining the sodium ion concentration in the blood plasma of the dialysis patient.

* * * * *